(12) United States Patent
Kim et al.

(10) Patent No.: US 11,185,852 B2
(45) Date of Patent: Nov. 30, 2021

(54) CATALYST COMPOSITION FOR HYDROFORMYLATION AND METHOD OF PREPARING ALDEHYDE USING THE SAME

(71) Applicant: LG CHEM, LTD., Seoul (KR)

(72) Inventors: Tae Yun Kim, Daejeon (KR); Min Ji Choi, Daejeon (KR); Sung Shik Eom, Daejeon (KR); Mi Young Kim, Daejeon (KR); Dong Hyun Ko, Daejeon (KR); Da Won Jung, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/306,839

(22) PCT Filed: Feb. 2, 2018

(86) PCT No.: PCT/KR2018/001429
§ 371 (c)(1),
(2) Date: Dec. 3, 2018

(87) PCT Pub. No.: WO2018/221830
PCT Pub. Date: Dec. 6, 2018

(65) Prior Publication Data
US 2021/0039079 A1 Feb. 11, 2021

(30) Foreign Application Priority Data

May 29, 2017 (KR) .................. 10-2017-0066187
Nov. 14, 2017 (KR) .................. 10-2017-0151202

(51) Int. Cl.
*C07C 45/50* (2006.01)
*B01J 31/00* (2006.01)
*B01J 31/18* (2006.01)
*B01J 31/20* (2006.01)
*B01J 31/22* (2006.01)

(52) U.S. Cl.
CPC .......... *B01J 31/185* (2013.01); *B01J 31/20* (2013.01); *B01J 31/2213* (2013.01); *C07C 45/505* (2013.01); *B01J 2231/321* (2013.01); *B01J 2531/004* (2013.01); *B01J 2531/822* (2013.01)

(58) Field of Classification Search
CPC ...... C07C 45/50; C07C 45/505; B01J 31/185; B01J 31/20
See application file for complete search history.

(56) References Cited

U.S. PATENT DOCUMENTS

| | | | |
|---|---|---|---|
| 8,598,390 B2 | 12/2013 | Eisenschmid et al. | |
| 8,664,451 B2 | 3/2014 | Eisenschmid et al. | |
| 9,221,850 B2 | 12/2015 | Dyballa et al. | |
| 9,695,098 B2 | 7/2017 | Miller et al. | |
| 9,707,552 B1 | 7/2017 | Kim et al. | |
| 9,914,681 B2 | 3/2018 | Geilen et al. | |
| 10,913,055 B2 | 2/2021 | Kim et al. | |
| 2012/0253080 A1 | 10/2012 | Eisenschmid et al. | |
| 2015/0328628 A1 | 11/2015 | Diebolt et al. | |
| 2015/0336988 A1 | 11/2015 | Dyballa et al. | |
| 2015/0336989 A1 | 11/2015 | Dyballa et al. | |
| 2017/0197201 A1 | 7/2017 | Kim et al. | |

FOREIGN PATENT DOCUMENTS

| CN | 102741209 | 10/2012 |
|---|---|---|
| CN | 102741210 | 10/2012 |
| CN | 104725170 | 6/2015 |
| CN | 105198699 | 12/2015 |
| CN | 106550597 | 3/2017 |
| CN | 106550697 | 4/2017 |
| CN | 108136381 | 6/2018 |
| EP | 3156127 A1 | 4/2017 |
| EP | 3482827 A1 | 5/2019 |
| JP | 2013515061 A | 5/2013 |
| JP | 5972427 | 8/2016 |
| KR | 101150557 B1 | 5/2012 |
| KR | 10-2017-0007906 | 1/2017 |
| KR | 10-2017-0007906 A | 1/2017 |
| KR | 1020180006299 A | 1/2018 |
| WO | 2011-087696 | 7/2011 |
| WO | 2018/008928 A1 | 1/2018 |

OTHER PUBLICATIONS

Kubis, et al., "A Comparative In Situ HP-FTIR Spectroscopic Study of Bi-and Monodentate Phosphite-Modified Hydroformylation", ChemCatChem 2010, 2, 287-295.
Van Rooy, et al., "Hydroformylation with a Rhodium/Bulky Phosphite Modified Catalyst. Catalyst Comparison for Oct-1-ene, Cyclohexene, and Styrene", Organometallics 1995, 14, 34-43.
Tricas et al., "Bulky monophosphite ligands for ethene hydroformylation," Journal of Catalysis 298: 198-205 (2013).
M. Clarke, "Rhodium catalysed hydroformylation of unsaturated esters," Tetrahedron Letters 45: 4043-4045 (2004).
Li, et al., "Comparative studies of triphenylphosphine and phosphite in the hydroformylation of dicyclopentadiene," Industrial Catalysis, 2013, 21(8):66-69.
Zhang, et al., "Hydrolysis Stability of Bidentate Phospites Utilized as Modifying Ligands in the Rh-Catalyzed n-Regioselective Hydroformylation of Olefins," ACS Catalysis 2016, 6, 755-7565.

*Primary Examiner* — Sikarl A Witherspoon
(74) *Attorney, Agent, or Firm* — Dentons US LLP

(57) ABSTRACT

The present invention relates to a catalyst composition for hydroformylation and a method of preparing an aldehyde using the same. More specifically, the present invention provides a catalyst composition for hydroformylation including a specific phosphite-based ligand and a transition metal compound in a specific amount range, thereby being capable of greatly lowering a use amount of an expensive transition metal compound and exhibiting excellent catalyst activity or stability. In addition, by using the catalyst composition in hydroformylation, excellent reaction efficiency may be provided and iso-aldehyde may be generated in high yield.

12 Claims, 1 Drawing Sheet

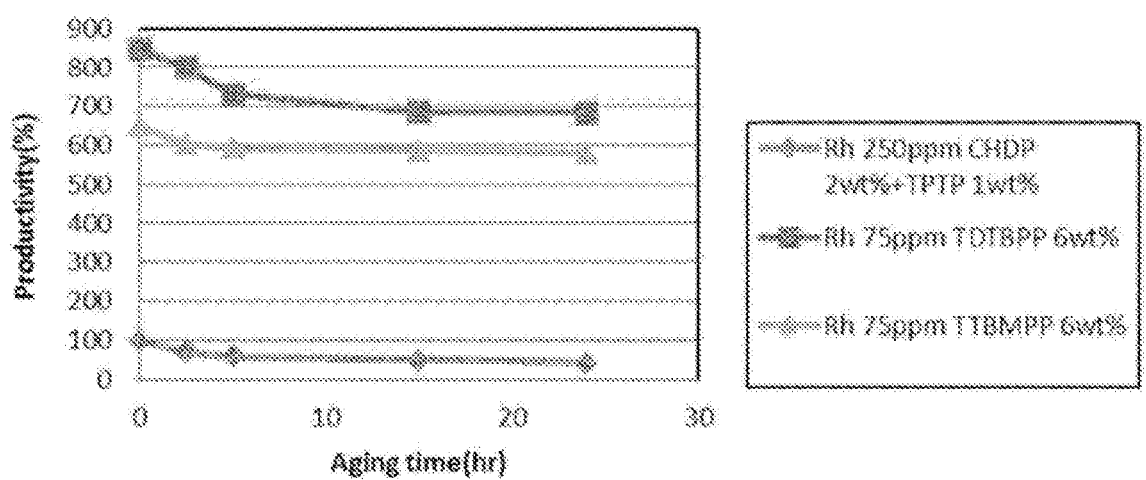

CATALYST COMPOSITION FOR HYDROFORMYLATION AND METHOD OF PREPARING ALDEHYDE USING THE SAME

CROSS-REFERENCE TO RELATED APPLICATIONS

This is a National Stage Application of International Application No. PCT/KR2018/001429, filed Feb. 2, 2018, which claims priority to Korean Patent Application No. 10-2017-0066187, filed on May 29, 2017, and Korean Patent Application No. 10-2017-0151202, re-filed on Nov. 14, 2017, based on the priority of the above patent, in the Korean Intellectual Property Office, the disclosures of each of which are incorporated herein by reference.

The present invention relates to a catalyst composition for hydroformylation and a method of preparing an aldehyde using the same. More specifically, the present invention relates to a catalyst composition for hydroformylation including a specific phosphite-based compound and a transition metal catalyst and a method of preparing an aldehyde having excellent selectivity to iso-aldehyde along with excellent catalyst activity or stability using the catalyst composition.

BACKGROUND ART

Hydroformylation, also known as oxo reaction, is a reaction of reacting various olefinic compounds with carbon monoxide (CO) and hydrogen ($H_2$), often referred to as synthesis gas, in the presence of a metal catalyst and a ligand to generate n-aldehyde and iso-aldehyde, the number of carbons of which is increased by one.

Aldehydes generated by oxo reaction may be oxidized or hydrogenated to be transformed into aldehyde derivatives, acids and alcohols, or may be condensation-reacted with aldol, etc. and then oxidized or hydrogenated to be transformed into various acids and alcohols containing long alkyl groups. Hydrogenated alcohols of aldehydes prepared by such oxo reaction are called oxo alcohols. These oxo alcohols are widely used for industrial purposes such as various solvents, additives, raw materials for plasticizers, and synthetic lubricants.

Conventionally, the value of n-aldehyde among products of hydroformylation was high, whereby most research on catalysts has been conducted to increase the proportion of n-aldehyde. However, recently, demand for iso-aldehyde is increasing due to development of, for example, isobutyric acid, neopentyl glycol (NPG), 2,2,4-trimethyl-1,3-pentanediol, and isovaleric acid prepared using iso-aldehyde derivatives as raw materials, whereby there is a need for development of a catalyst system having excellent reaction activity and stability while increasing the proportion of iso-aldehyde.

[Prior Art Documents]
[Patent Document] (Patent Document 1) JP 2013-515061 A
(Patent Document 2) KR 1150557 B1

DISCLOSURE

Technical Problem

Therefore, the present invention has been made in view of the above problems, and it is one object of the present invention to provide a catalyst composition for hydroformylation exhibiting excellent catalyst stability and activity despite use of a small amount of expensive transition metal catalyst compared to conventional cases.

It is another object of the present invention to provide a method of preparing aldehyde, the method being capable of providing iso-aldehyde in high yield due to a low N/I selectivity of 1.7 or less by reacting an olefinic compound with syngas (CO/$H_2$) in the presence of the catalyst composition.

The above and other objects can be accomplished by the present disclosure described below.

Technical Solution

In accordance with one aspect of the present invention, provided is a catalyst composition for hydroformylation including a phosphite-based ligand represented by Formula 1 below; a transition metal compound represented by Formula 2 below; and a solvent, wherein the transition metal is included in a content of greater than 30 ppm and 100 ppm or less based on a total weight of the phosphite-based ligand, the transition metal compound, and the solvent:

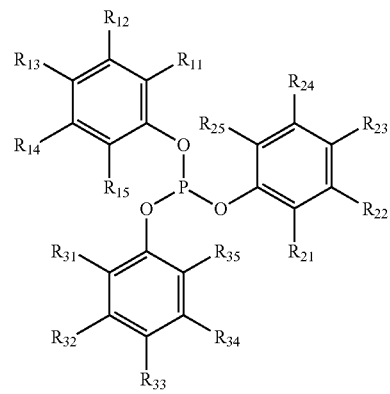

[Formula 1]

wherein $R_{11}$ to $R_{15}$, $R_{21}$ to $R_{25}$ and $R_{31}$ to $R_{35}$ are the same or different and are each independently selected from among hydrogen, normal alkyl groups having 1 to 20 carbon atoms, and branched alkyl groups having 4 to 20 carbon atoms, and $$M(L^1)_x(L^2)_y(L^3)_z \qquad \text{Formula 2}$$

wherein M is one selected from the group consisting of rhodium (Rh), cobalt (Co), iridium (Ir), ruthenium (Ru), iron (Fe), nickel (Ni), palladium (Pd), platinum (Pt), and osmium (Os), $L^1$, $L^2$, and $L^3$ are each independently one selected from the group consisting of hydrogen, carbonyl (CO), cyclooctadiene, norbornene, chlorine, triphenylphosphine (TPP), and acetylacetonate (AcAc), x, y, and z are each independently an integer of 0 to 5, and x, y and z are not 0 at the same time.

In accordance with another aspect of the present invention, provided is a method of preparing aldehyde, the method including a hydroformylation step of reacting an olefinic compound with syngas (CO/$H_2$) in the presence of the catalyst composition to prepare aldehyde.

Advantageous Effects

As apparent from the foregoing, the present invention advantageously provides a catalyst composition for hydroformylation exhibiting high activity and maintaining high activity over a long period of time despite use of a small amount of expressive transition metal compound at a level of 30% as compared to conventional cases and, accordingly, having economic advantages. In addition, aldehyde obtained by applying the catalyst composition to a hydroformylation process of olefin exhibits an N/I selectivity of 1.7 or less, thereby generating iso-aldehyde in high yield.

DESCRIPTION OF DRAWINGS

The FIGURE is a graph illustrating stability (productivity) test results of catalyst compositions according to examples and comparative examples.

BEST MODE

Hereinafter, a catalyst composition for hydroformylation of the present invention is described in detail.

The present inventors attempted to address the problem that stability is decreased and, accordingly, the lifespan of a catalyst is shortened although selectivity to iso-aldehyde is high and high activity is exhibited in an initial stage in the case of a conventional catalyst system including a rhodium catalyst and a phosphite-based ligand. As a result, the present inventors confirmed that, when a specific phosphite-based ligand and a rhodium catalyst are used in a specific amount range, the expensive rhodium catalyst may be used in a small content compared to conventional cases, the activity of the catalyst may be highly maintained, long-term stability may be improved, and, when the specific phosphite-based ligand and the rhodium catalyst, which are used in a specific amount range, are used in hydroformylation of propene, excellent iso-butyraldehyde selectivity is exhibited. Based on these findings, the present inventors continued further study and completed the present invention.

The catalyst composition for hydroformylation of the present invention includes a phosphite-based ligand represented by Formula 1 below; a transition metal compound; and a solvent, wherein the transition metal is included in a content of greater than 30 ppm and 100 ppm or less based on a total weight of the phosphite-based ligand, the transition metal compound, and the solvent.

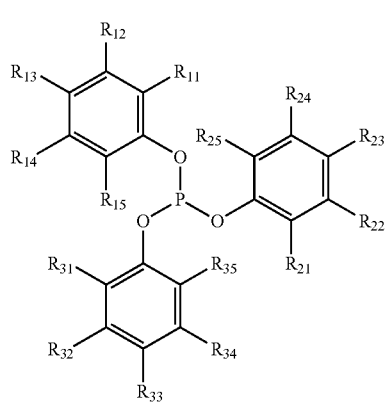

[Formula 1]

In Formula 1, $R_{11}$ to $R_{15}$, $R_{21}$ to $R_{25}$ and $R_{31}$ to $R_{35}$ are the same or different and are each independently selected from among hydrogen, normal alkyl groups having 1 to 20 carbon atoms, and branched alkyl groups having 4 to 20 carbon atoms.

As a preferred example, in the phosphite-based ligand represented by Formula 1, each of $R_{11}$, $R_{13}$, $R_{21}$, $R_{23}$, $R_{31}$, and $R_{33}$ is a branched alkyl having 4 to 10 carbon atoms. More preferably, each of $R_{11}$, $R_{13}$, $R_{21}$, $R_{23}$, $R_{31}$, and $R_{33}$ is tert-butyl (t-Bu). In this case, when the phosphite-based ligand is applied to hydroformylation of an olefin compound, selectivity to iso-aldehyde may be excellent, and stability or activity of the catalyst may be excellent.

As another example, in the phosphite-based ligand represented by Formula 1, each of $R_{11}$, $R_{21}$, and $R_{31}$ may be a branched alkyl group having 4 to 10 carbon atoms, and each of $R_{41}$, $R_{23}$, and $R_{33}$ may be a normal alkyl group having 1 to 10 carbon atoms. More preferably, each of $R_{11}$, $R_{21}$, and $R_{31}$ is tert-butyl (t-Bu), and each of $R_{13}$, $R_{23}$, and $R_{33}$ is a normal alkyl group having 1 to 3 carbon atoms. In this case, when the phosphite-based ligand is applied to hydroformylation of an olefin compound, selectivity to iso-aldehyde may be excellent, and stability or activity of the catalyst may be excellent.

As a more specific example, the phosphite-based ligand represented by Formula 1 may be tris(2,4-di-tert-butylphenyl)phosphite represented by Formula 1a below or tris(2-tert-butyl-4-methylphenyl)phosphite represented by Formula 1b below. More preferably, the phosphite-based ligand represented by Formula 1 is a compound represented by Formula 1a. In these cases, even when the transition metal compound is used in a small amount, activity or stability of the catalyst may be highly maintained, and, when the phosphite-based ligand represented by Formula 1 is used in hydroformylation of olefin, excellent selectivity to iso-aldehyde may exhibited:

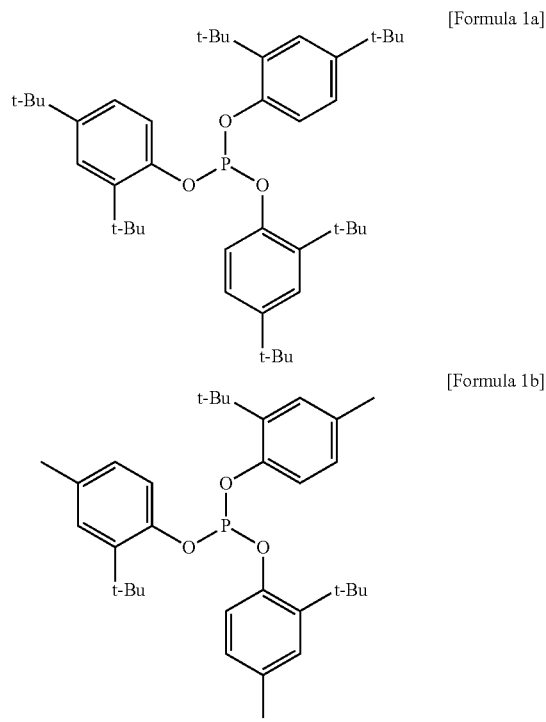

The phosphite-based ligand represented by Formula 1 may be included in an amount of, for example, 2 to 10% by weight, 2 to 8% by weight, 3 to 6% by weight, 3 to 5% by weight, 3 to 4.5% by weight, 4 to 7% by weight, or 4 to 6% by weight, based on 100% by weight of a catalyst composition including the phosphite-based ligand, a transition metal compound, and a solvent. Within these ranges, stability, activity, etc. of the catalyst may be highly maintained while lowering a use amount of the transition metal compound and, when the catalyst composition is used in hydroformylation, excellent selectivity to iso-aldehyde may be exhibited.

The transition metal compound may be a compound represented by Formula 2 below:

$$M(L^1)_x(L^2)_y(L^3)_z \qquad \text{Formula 2}$$

wherein M is one selected from the group consisting of rhodium (Rh), cobalt (Co), iridium (Ir), ruthenium (Ru), iron (Fe), nickel (Ni), palladium (Pd), platinum (Pt), and osmium (Os), $L^1$, $L^2$, and $L^3$ are each independently one selected from the group consisting of hydrogen, carbonyl (CO), cyclooctadiene, norbornene, chlorine, triphenylphosphine (TPP), and acetylacetonate (AcAc), x, y, and z are each independently an integer of 0 to 5, and x, y and z are not 0 at the same time.

As a more specific example, the transition metal compound may be one or more selected from the group consisting of (acetylacetonato)dicarbonylrhodium [Rh(AcAc)(CO)$_2$], (acetylacetonato)carbonyl(triphenylphosphine)rhodium [Rh(AcAc)(CO)(TPP)], hydridocarbonyltris(triphenylphosphine)rhodium [HRh(CO)(TPP)$_3$], cobaltcarbonyl [Co$_2$(CO)$_8$], (acetylacetonato)carbonyliridium [Ir(AcAc)(CO)$_2$], and hydridocarbonyltris(triphenylphosphine)iridium [HIr(CO)(TPP)$_3$], but the present invention is not limited thereto.

For example, the transition metal is preferably included in an amount of greater than 30 ppm and 100 ppm or less, 35 to 100 ppm, 40 to 100 ppm, 45 to 100 ppm, 50 to 100 ppm, 50 to 90 ppm, 50 to 80 ppm, 60 to 80 ppm, or 70 to 80 ppm based on a total weight of a catalyst composition including the phosphite-based ligand represented by Formula 1, a transition metal compound, and a solvent. Within these ranges, activity or stability of the catalyst may be high while using a small amount of expensive transition metal compound.

A molar ratio (L/M) of the phosphite-based ligand to the transition metal compound included in the catalyst composition of the present invention may be, for example, 32 to 320, 35 to 320, 40 to 238, 60 to 238, 60 to 230, 70 to 230, 100 to 230, 120 to 230, or 150 to 230. In this case, stability or activity of the catalyst may be highly maintained while lowering a use amount of the transition metal compound and, when the catalyst composition is used in hydroformylation, excellent selectivity to iso-aldehyde may be exhibited.

As a preferred example, the catalyst composition of the present invention may be a composition free from one coordinated phosphine ligand. In this case, stability, activity, etc. of the catalyst may be excellent and excellent selectivity to iso-aldehyde may be provided while greatly lowering a use amount of the transition metal compound compared to conventional cases.

In the present invention, the expression "free from one coordinated phosphine ligand" refers to the case wherein one coordinated phosphine ligand is intentionally omitted.

For example, the one coordinated phosphine ligand may be a compound represented by Formula 4 below:

[Formula 4]

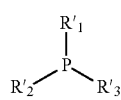

wherein $R'_1$, $R'_2$ and $R'_3$ are the same or different and are each independently a substituted or unsubstituted C1 to C20 alkyl group; a substituted or unsubstituted C5 to C20 cycloalkyl or cycloalkenyl group; a substituted or unsubstituted C6 to C36 aryl group; a substituted or unsubstituted C1 to C20 heteroalkyl group; a substituted or unsubstituted C4 to C36 heteroaryl group; or a substituted or unsubstituted C4 to C36 heterocyclic group. Each of the heteroalkyl group, the heteroaryl group, and the heterocyclic group may contain, for example, one or more atoms selected from the group consisting of N, O, and S. When $R'_1$, $R'_2$ and $R'_3$ are substituted with a substituent, the substituent may be, for example, a nitro group (—NO$_2$), fluorine (—F), chlorine (—Cl), bromine (—Br), or a C1 to C20 alkyl group.

As a more preferable example, the catalyst composition of the present invention may be a single ligand system only including the phosphite-based ligand represented by Formula 1 as a ligand. In this case, costs may be considerably reduced by lowering the content of the transition metal compound, activity, stability, etc. of the catalyst may be excellent, and excellent selectivity to iso-aldehyde may be exhibited.

As a most preferable example, the catalyst composition of the present invention includes tris(2,4-di-tert-butylphenyl)phosphite and/or tris(2-tert-butyl-4-methylphenyl)phosphite, as the phosphite-based ligand represented by Formula 1 and is a composition free from one coordinated phosphine ligand. In this case, despite application of a small amount of transition metal compound, activity or stability of the catalyst is considerably excellent and excellent selectivity to iso-aldehyde is exhibited.

As another preferable example, the catalyst composition of the present invention includes the phosphite-based ligand represented by Formula 1; the transition metal compound represented by Formula 2; and a solvent. Here, the content of the transition metal may be greater than 30 ppm and 100 ppm or less based on a total weight of the phosphite-based ligand, the transition metal compound, and the solvent. In this case, a use amount of the expensive transition metal compound is greatly lowered, and stability and activity of the catalyst and selectivity to iso-aldehyde are excellent.

Here, the phosphite-based ligand represented by Formula 1 is preferably tris(2,4-di-tert-butylphenyl)phosphite and/or tris(2-tert-butyl-4-methylphenyl)phosphite in terms of activity or stability of a catalyst or selectivity to iso-aldehyde.

The solvent may be, for example, one or more selected from the group consisting of propionaldehyde, butyraldehyde, pentyl aldehyde, acetone, methyl ethyl ketone, methyl isobutyl ketone, acetophenone, cyclohexanone, ethanol, pentanol, octanol, texanol, benzene, toluene, xylene, orthodichlorobenzene, tetrahydrofuran, dimethoxyethane, dioxane, methylene chloride, and heptane.

As a preferred example, the solvent is an aldehyde such as propionaldehyde, butyraldehyde, or pentyl aldehyde. More preferably, a compound the same as the aldehyde generated by hydroformylation is used. In this case, a product may be easily isolated and improved purity is provided.

The catalyst composition for hydroformylation may be, for example, a catalyst composition used to produce butyraldehyde from propene.

As a specific example, the catalyst composition may generate n-butyraldehyde and iso-butyraldehyde in a molar ratio of 1.7 or less, 1.0 to 1.7, 1.5 or less, 1.2 to 1.5, or 1.2 to 1.3. That is, the catalyst composition may generate iso-butyraldehyde in high yield.

The catalyst composition may be used in hydroformylation. Hereinafter, a method of preparing aldehyde by reacting an olefinic compound with syngas in the presence of the catalyst composition for hydroformylation is described.

The method of preparing aldehyde of the present invention may include a hydroformylation step of reacting an olefinic compound with syngas (CO/H2) in the presence of the catalyst composition for hydroformylation to prepare aldehyde.

In the present invention, the olefinic compound may be, for example, a compound represented by Formula 3 below:

[Formula 3]

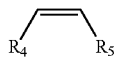

wherein $R_4$ and $R_5$ are each independently hydrogen, an alkyl group having 1 to 20 carbon atoms, fluorine (—F), chlorine (—Cl), bromine (—Br), a trifluoromethyl group (—CF$_3$), an unsubstituted C6 to C20 aryl group, or a C6 to C20 aryl group substituted with 1 to 5 substituents. Here, the substituents of the aryl group are selected from among a nitro group (—NO$_2$), fluorine (—F), chlorine (—Cl), bromine (—Br), and a C1 to C5 alkyl group.

As a specific example, the olefinic compound may be one or more selected from the group consisting of ethene, propene, 1-butene, 1-pentene, 1-hexene, 1-octene, and styrene, but the present invention is not limited thereto.

As a more preferable example, the olefinic compound may be propene, and the aldehyde may be butyraldehyde. When the catalyst composition according to the present invention is used in hydroformylation of propene, a molar ratio of n-butyraldehyde to iso-butyraldehyde is low, i.e., the molar ratio is 1.7 or less, or 1.5 or less. Accordingly, iso-butyraldehyde may be generated in high yield.

A molar ratio of carbon monoxide (CO) to hydrogen (H$_2$) in the syngas may be, for example, 5:95 to 70:30, 40:60 to 60:40, or 45:55 to 55:45. Within these ranges, the gas used for the reaction is not accumulated in a reactor and excellent reaction balance is exhibited.

In the present invention, the hydroformylation is preferably carried out, for example, at 20 to 180° C., 50 to 150° C., 60 to 125° C., 70 to 100° C., 70 to 90° C., or 80 to 90° C. Within these ranges, stability and activity of the catalyst are excellent, the reaction may rapidly proceed, and side reactions, such as decomposition of a ligand, may be minimized.

In addition, the hydroformylation of the present invention is preferably carried out, for example, under a pressure condition of 1 to 100 bar, 1 to 500 bar, 5 to 30 bar, 5 to 13 bar, 5 to 9 bar, or 14 to 20 bar. Within these ranges, the risk of explosion is low, and aldehyde may be obtained in high yield due to rapid hydroformylation.

Hereinafter, the present invention will be described in more detail with reference to the following preferred examples. However, these examples are provided for illustrative purposes only and should not be construed as limiting the scope and spirit of the present invention. In addition, it will be apparent to those skilled in the art that various changes and modifications may be made without departing from the spirit and scope of the present invention, and such changes and modifications are also within the scope of the appended claims.

EXAMPLE

Example 1

1. Preparation of catalyst composition 0.024 g (0.049 mmol) of (acetylacetonato) carbonyl(triphenylphosphine) rhodium [Rh(AcAc)(CO)(TPP), ROPAC], as a catalyst, and tris(2,4-di-tert-butylphenyl) phosphite (TDTBPP), as a ligand, were dissolved in a butyraldehyde solvent such that a total weight of resultant solution reached 100.5 g (50 ppm of Rh, 6% by weight of TDTBPP), followed by feeding the same into an autoclave. The air was replaced with nitrogen while stirring the reaction solution. Subsequently, a gas mixture prepared by mixing propene and syngas (CO/H$_2$) in a molar ratio of 1:1:1 (C$_3$H$_6$:CO:H$_2$) was injected into the reaction solution, the pressure in the autoclave was maintained at 8 bar, and reaction was carried out while stirring at 90° C. for 1 hour.

Examples 2 to 8, Comparative Examples 1 to 7, and Reference Examples 1 to 4

Experiments were carried out in the same manner as in Example 1, except that the content of ROPAC and the content and type of ligand were changed as summarized in Table 1 below.

TEST EXAMPLE

WI selectivity, catalyst activity, and stability of aldehyde prepared according to each of Examples 1 to 8, Comparative Examples 1 to 7, and Reference Examples 1 to 4 were measured according to the following methods. Results are summarized in Tables 1 and 2 below and illustrated in the accompanying the FIGURE.

Test Example 1: N/I Selectivity

The amount of n-butyraldehyde produced by hydroformylation was divided by the amount of iso-butyraldehyde. A generation amount of each aldehyde was determined by gas chromatography (GC).

Test Example 2: Activity of Catalyst

A total weight of n-butyraldehyde and iso-butyraldehyde produced through reaction using the catalyst according to each of the examples, the comparative examples, and the reference examples was compared to 100% of a total weight of n-butyraldehyde and iso-butyraldehyde produced through reaction (reaction pressure: 8 bar, reaction temperature: 90° C.) using the catalyst according to Comparative Example 1. Catalyst activity was calculated according to Equation 1 below, and represented as a percentage:

[Equation 1]

Catalyst activity (%)=(Total weight of n-butyraldehyde and iso-butyraldehyde according to example, comparative example, or reference example/total weight of n-butyraldehyde and iso-butyraldehyde according to Comparative Example 1)×100

TABLE 1

| Classification | Ligand type | Ligand content (% by weight) | Rhodium use amount (ppm) | N/I selectivity | Catalyst activity (%) |
|---|---|---|---|---|---|
| Example 1 | TDTBPP | 3 | 50 | 1.2~1.6 | 788 |
| Example 2 | TDTBPP | 6 | 50 | 1.2~1.6 | 788 |
| Example 3 | TDTBPP | 4.5 | 75 | 1.2~1.6 | 863 |
| Example 4 | TDTBPP | 6 | 75 | 1.2~1.6 | 846 |
| Example 5 | TDTBPP | 3 | 100 | 1.2~1.6 | 954 |
| Example 6 | TDTBPP | 6 | 100 | 1.2~1.6 | 1084 |
| Example 7 | TTBMPP | 3 | 50 | 1.3~1.7 | 680 |
| Example 8 | TTBMPP | 6 | 75 | 1.3~1.7 | 650 |
| Comparative Example 1 | CHDP + TPTP | 3[a] | 250 | 3.5 | 100 |
| Comparative Example 2 | CHDP | 2 | 250 | 2.5 | 96 |
| Comparative Example 3 | TPTP | 3 | 250 | 6 | 130 |
| Comparative Example 4 | TDTBPP | 3 | 250 | 1.8 | 1200 |
| Comparative Example 5 | TDTBPP | 10 | 250 | 2 | 1178 |
| Comparative Example 6 | TTBMPP | 6 | 250 | 1.9 | 604 |
| Comparative Example 7 | TDTBPP | 6 | 30 | 1.3 | 270 |
| Reference Example 1 | TDTBPP + CHDP | 3[b] | 250 | 2 | 105 |
| Reference Example 2 | TDTBPP + CHDP | 3[c] | 100 | 2.2 | 60 |
| Reference Example 3 | TDTBPP + TPTP | 3[d] | 250 | 2.4 | 225 |
| Reference Example 4 | TDTBPP + TPTP | 3[e] | 100 | 2.6 | 76 |

[a]Mixture of 2% by weight of CHDP and 1% by weight of TPTP
[b]Mixture of 2% by weight of TDTBPP and 1% by weight of CHDP
[c]Mixture of 2% by weight of TDTBPP and 1% by weight of CHDP
[d]Mixture of 2% by weight of TDTBPP and 1% by weight of TPTP
[e]Mixture of 2% by weight of TDTBPP and 1% by weight of TPTP
** TTBMPP: Tris(2-tert-butyl-4-methylphenyl)phosphite
* CHDP: Cyclohexyldiphenylphosphine
* TPTP: Tri-p-tolylphosphine As shown in Table 1, it can be confirmed that, when hydroformylation is carried out using the catalyst composition of the present invention, N/I selectivity is 1.7 or less, i.e., selectivity to iso butyraldehyde is high, and catalyst activity is excellent although the amount of rhodium is about 20 to 40% of those of Comparative Examples 1 to 6.

In addition, it can be confirmed that, when the catalyst composition of each of Comparative Examples 4 to 6, in which TDTBPP or TTBMPP, as a ligand, is used in the same content as in the examples, but the content of rhodium is 250 ppm, i.e., the rhodium content is excessively high, is used in hydroformylation, N/I selectivity exceeds a desired value. On the other hand, it can be confirmed that, when the catalyst composition of Comparative Example 7, in which the content of rhodium is 30 ppm, i.e., the rhodium content is low, is used in hydroformylation, selectivity to iso butyraldehyde is excellent, but catalyst activity is considerably decreased.

Meanwhile, it can be confirmed that, when TDTBPP or TTBMPP is included as a ligand, but one coordinated phosphine ligand, i.e., TPTP or CHDP, is mixed, N/I selectivity greatly exceeds a desired value, and catalyst activity is also considerably decreased. In addition, it can be confirmed that, when the content of rhodium is controlled to 100 ppm, i.e., controlled in the range according to the present invention (Reference Examples 2 and 4), stability is further decreased and thus very poor.

Test Example 3: Catalyst Stability (Productivity)

Syngas (CO/$H_2$) mixed in a molar ratio of 1:1 was injected into the reaction solution until the pressure of a reactor reached 6.05 bar, followed by aging while stirring at 118.9° C. for 0 hours, 2.5 hours, 5 hours, 15 hours, and 24 hours, and then cooling to 20° C. Subsequently, the syngas was substituted with a gas mixture of propene ($C_3H_6$) and syngas (CO/$H_2$) mixed in a molar ratio of 1:1:1 ($C_3H_6$:CO:$H_2$). Subsequently, reaction was allowed for one hour while maintaining the pressure inside the reactor at 8 bar and stirring at 90° C., followed by calculating catalyst activity. Results are summarized in Table 2 below and the accompanying FIG. 1 the FIGURE.

TABLE 2

| Classification | Catalyst stability (productivity) test | | | | |
|---|---|---|---|---|---|
| | 0 hr | 2.5 hr | 5 hr | 15 hr | 24 hr |
| Example 1 | 788 | 521 | 475 | 444 | 398 |
| Example 2 | 788 | 626 | 594 | 579 | 550 |
| Example 3 | 863 | 580 | 510 | 398 | 396 |
| Example 4 | 846 | 800 | 731 | 686 | 684 |
| Example 5 | 954 | 611 | 506 | 348 | 336 |
| Example 6 | 1084 | 914 | 888 | 808 | 492 |
| Example 7 | 680 | 518 | 457 | 434 | 387 |
| Example 8 | 650 | 602 | 592 | 586 | 580 |
| Comparative Example 1 | 100 | 70 | 58 | 49 | 43 |
| Comparative Example 2 | 96 | 87 | 59 | 52 | 52 |
| Comparative Example 3 | 130 | 66 | 5 | 40 | 28 |
| Comparative Example 4 | 1200 | 754 | 224 | 177 | 6 |
| Comparative Example 5 | 1178 | 771 | 392 | 277 | 167 |
| Comparative Example 6 | 604 | 363 | 195 | 161 | 85 |
| Comparative Example 7 | 270 | 150 | 120 | 115 | 94 |
| Reference Example 1 | 105 | 87 | 84 | 80 | 78 |
| Reference Example 2 | 60 | 54 | 53 | 51 | 50 |
| Reference Example 3 | 225 | 187 | 160 | 138 | 126 |
| Reference Example 4 | 76 | 60 | 58 | 50 | 46 |

As shown in Table 2 and the FIGURE, it can be confirmed that, although the content of rhodium in the catalyst compositions according to Examples 1 to 8 is about 20 to 40% of those of Comparative Examples 1 to 6, initial catalyst activity is excellent, long-term stability of the catalyst is excellent, and, particularly, catalyst activity is 300% or more, i.e., catalyst activity is highly maintained, also after aging over a period of 24 hours.

In addition, it can be confirmed that, in the case of the catalyst composition of Comparative Example 7 in which rhodium is included in a smaller amount compared to the catalyst composition according to the present invention, catalyst activity is considerably decreased after aging, i.e., catalyst stability is poor.

On the other hand, it can be confirmed that, in the case of Comparative Examples 1 to 3 in which ligands not according to the present invention are used, initial catalyst activity and stability are poor although the content of rhodium is considerably excessive compared to the examples. In addition, it can be confirmed that, in the case of Comparative Example 4 to 6 in which a ligand not according to the present invention is used, the catalyst compositions exhibit excellent initial catalyst activity, but catalyst stability is rapidly decreased.

Further, it can be confirmed that, in the case of Reference Examples 1 to 4 in which a mixture of a phosphite-based ligand and one coordinated phosphine ligand is used, initial catalyst activity is very poor as described above, and catalyst activity is further decreased after aging over a period of 24 hours.

The invention claimed is:

1. A catalyst composition for hydroformylation, comprising:
   a phosphite-based ligand of Formula 1 below;
   a transition metal compound of Formula 2 below; and
   a solvent comprising at least one selected from the group consisting of propionaldehyde, butyraldehyde, pentyl aldehyde, acetophenone, cyclohexanone, ethanol, pentanol, octanol, texanol, orthodichlorobenzene, tetrahydrofuran, dimethoxyethane, and dioxane,
   wherein the transition metal is present in an amount of 50 to 90 ppm based on a total weight of the catalyst composition:

[Formula 1]

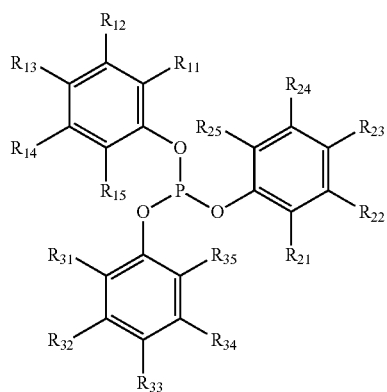

wherein $R_{11}$ to $R_{15}$, $R_{21}$ to $R_{25}$ and $R_{31}$ to $R_{35}$ are the same or different and are each independently selected from among hydrogen, unbranched alkyl groups having 1 to 20 carbon atoms, and branched alkyl groups having 4 to 20 carbon atoms, and $$M(L^1)_x(L^2)_y(L^3)_z \qquad \text{Formula 2}$$

wherein M is selected from the group consisting of rhodium (Rh), cobalt (Co), iridium (Ir), ruthenium (Ru), iron (Fe), nickel (Ni), palladium (Pd), platinum (Pt), and osmium (Os); $L^1$, $L^2$, and $L^3$ are each independently selected from the group consisting of hydrogen, carbonyl (CO), cyclooctadiene, norbornene, chlorine, triphenylphosphine (TPP), and acetylacetonate (AcAc); x, y, and z are each independently an integer of 0 to 5, and x, y and z are not 0 at the same time,
wherein the phosphite-based ligand is present in an amount of 2 to 8% by weight based on 100% by weight of the catalyst composition, and
wherein a molar ratio (L/M) of the phosphite-based ligand to the transition metal compound is 60 to 230.

2. The catalyst composition according to claim 1, wherein in Formula 1, each of $R_{11}$, $R_{13}$, $R_{21}$, $R_{23}$, $R_{31}$, and $R_{33}$ is a branched alkyl group having 4 to 10 carbon atoms.

3. The catalyst composition according to claim 1, wherein in Formula 1, each of $R_{11}$, $R_{21}$, and $R_{31}$ is a branched alkyl group having 4 to 10 carbon atoms, and each of $R_{13}$, $R_{23}$, and $R_{33}$ is an unbranched alkyl group having 1 to 10 carbon atoms.

4. The catalyst composition according to claim 1, wherein the transition metal compound is at least one selected from the group consisting of (acetylacetonato)dicarbonylrhodium [Rh(AcAc)(CO)$_2$], (acetylacetonato)carbonyl-(triphenylphosphine)rhodium [Rh(AcAc)(CO)(TPP)], hydridocarbonyltris-(triphenylphosphine)rhodium [HRh(CO)(TPP)$_3$], cobaltcarbonyl [CO$_2$(CO)$_8$], (acetylacetonato)carbonyliridium [Ir(AcAc)(CO)$_2$], and hydridocarbonyltris-(triphenylphosphine)iridium [HIr(CO)(TPP)$_3$].

5. A method of preparing butyraldehyde, the method comprising a hydroformylation step of reacting propene with syngas (CO/H$_2$) in the presence of the catalyst composition according to claim 1,
   wherein the butyraldehyde is a mixture of n-butyraldehyde and iso-butyraldehyde, and the n-butyraldehyde/iso-butyraldehyde selectivity is 1.7 or less.

6. The method according to claim 5, wherein the syngas comprises a mixture of carbon monoxide (CO) and hydrogen (H$_2$), wherein the carbon monoxide and hydrogen are mixed in a molar ratio of 5:95 to 70:30.

7. The method according to claim 5, wherein the hydroformylation step is carried out at a reaction temperature of 20 to 180° C. and a pressure of 1 to 100 bar.

8. The catalyst composition according to claim 1, wherein the solvent comprises at least one selected from the group consisting of propionaldehyde, butyraldehyde, and pentyl aldehyde.

9. The catalyst composition according to claim 8, wherein the transition metal compound is (acetylacetonato)carbonyl (triphenylphosphine)rhodium [Rh(acac)(CO)(TPP)].

10. The catalyst composition according to claim 9, wherein the phosphite-based ligand is tris(2,4-di-tert-butylphenyl)phosphite (TDTBPP).

11. The method of claim 5, wherein the catalyst composition comprises butyraldehyde as the solvent.

12. The catalyst composition according to claim 1, wherein the transition metal is present in an amount of 50 to 80 ppm based on a total weight of the catalyst composition.

* * * * *

UNITED STATES PATENT AND TRADEMARK OFFICE
CERTIFICATE OF CORRECTION

PATENT NO. : 11,185,852 B2
APPLICATION NO. : 16/306839
DATED : November 30, 2021
INVENTOR(S) : Kim et al.

It is certified that error appears in the above-identified patent and that said Letters Patent is hereby corrected as shown below:

In the Claims

At Column 12, Lines 16-24, please replace Claim 4 with the following:
4. The catalyst composition according to claim 1, wherein the transition metal compound is at least one selected from the group consisting of (acetylacetonato)dicarbonylrhodium [$Rh(AcAc)(CO)_2$], (acetylacetonato)carbonyl-(triphenylphosphine)rhodium [$Rh(AcAc)(CO)(TPP)$], hydridocarbonyltris-(triphenylphosphine)rhodium [$HRh(CO)(TPP)_3$], cobaltcarbonyl [$Co_2(CO)_8$], (acetylacetonato)carbonyliridium [$Ir(AcAc)(CO)_2$], and hydridocarbonyltris-(triphenylphosphine)iridium [$HIr(CO)(TPP)_3$].

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*